(12) United States Patent
Rey

(10) Patent No.: US 12,239,615 B2
(45) Date of Patent: *Mar. 4, 2025

(54) HYDROXYNORKETAMINE FOR THE USE IN THE TREATMENT OF DEPRESSION

(71) Applicant: KETABON GMBH, Munich (DE)

(72) Inventor: Helene Rey, Pratteln (CH)

(73) Assignee: Ketabon GmbH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/212,375

(22) Filed: Jun. 21, 2023

(65) Prior Publication Data

US 2023/0330043 A1  Oct. 19, 2023

Related U.S. Application Data

(63) Continuation of application No. 16/625,845, filed as application No. PCT/EP2018/066823 on Jun. 22, 2018, now Pat. No. 11,723,883.

(30) Foreign Application Priority Data

Jun. 23, 2017 (EP) .................................... 17177660

(51) Int. Cl.
*A61K 31/135* (2006.01)
*A61K 9/28* (2006.01)

(52) U.S. Cl.
CPC .......... *A61K 31/135* (2013.01); *A61K 9/2866* (2013.01)

(58) Field of Classification Search
CPC ........................... A61K 31/135; A61K 9/2866
USPC .......................................................... 514/647
See application file for complete search history.

(56) References Cited

U.S. PATENT DOCUMENTS 11,723,883 B2 * 8/2023 Rey ..................... A61K 9/5073
514/647

* cited by examiner

*Primary Examiner* — Kristin A Vajda
(74) *Attorney, Agent, or Firm* — Daniel S. Kim

(57) ABSTRACT

The present invention relates to hydroxynorketamine for the use in the treatment of depression. In particular, the present invention concerns hydroxynorketamine for use in the treatment of depression, wherein hydroxynorketamine is administered in form of at least one prodrug, and wherein the at least one prodrug is orally administered in a modified-release dosage form.

18 Claims, No Drawings

HYDROXYNORKETAMINE FOR THE USE IN THE TREATMENT OF DEPRESSION

The present invention relates to hydroxynorketamine for the use in the treatment of depression. In particular, the present invention concerns hydroxynorketamine for use in the treatment of depression, wherein hydroxynorketamine is administered in form of at least one prodrug, and wherein the at least one prodrug is orally administered in a modified-release dosage form.

Depression is a serious and often occurring disease. Around 16% of the world population suffer at some point in their lives from a major depressive disorder. Such disorder not only results in serious health but also in socioeconomic consequences. In addition, current pharmacotherapies usually require prolonged administration until any clinical improvement is observable. Such long lag time and an additionally high non-response rate show that there is an urgent need for a successful antidepressant therapy (Zanos et al., NMDAR inhibition-independent antidepressant actions of ketamine metabolites, Nature, 2016, 533: 481-486).

Ketamine is a chiral phencyclidine derivative with the IUPAC name 2-(2-chlorophenyl)-2-(methylamino) cyclohexan-1-one. Ketamine was initially developed in the 1970' as a short acting anaesthetic agent (Moaddel et al., Subchronic administration of (R,S)-ketamine induces ketamine ring hydroxylation in Wistar rats, 2016, Journal of Pharmaceutical and Biomedical Analysis, 127, 3-8).

Ketamine acts as a non-competitive, glutamergic NMDAR-antagonist. Additionally, it has been shown that a single intravenous administration in form of a 40-minute infusion of the ketamine hydrochloride results in rapid improvement in patients with major depressive disorder and bipolar depression lasting 1 week (Zarate et al., Relationship of Ketamine's Plasma Metabolites with Response, Diagnosis, and Side Effects in Major Depression, 2012, Biol. Psychiatry, 72(4): 331-338).

Due to undesirable side effects, such as abuse liability and capacity to produce dissociative effect, the potential of ketamine for clinical use, however, is limited. Recent investigation of the antidepressant effect of intraperitoneal administered (R,S)-ketamine revealed that the metabolism of (R,S)-ketamine into (2S,6S;2R,6R)-hydroxynorketamine is essential for the antidepressant effect. Thereby, it was shown that the (2R,6R)-hydroxynorketamine enantiomer exerts antidepressant-related actions in mice, which are independent of NMDR-inhibition and lack ketamine-related side effects (Zanos et al., NMDAR inhibition-independent antidepressant actions of ketamine metabolites, Nature, 2016, 533: 481486).

WO 2013/056229 discloses various pharmaceutical preparations containing ketamine metabolites and/or prodrugs of ketamine metabolites for use in the treatment of bipolar depression, major depressive disorder, schizophrenia. Alzheimer's dementia, amyotrophic lateral sclerosis, complex regional pain syndrome (CRPS), chronic pain or neuropathic pain. However. WO 2013/056229 relates to each appropriate route of administration and does not address specific dosage forms suitable for the treatment of depression.

In order to provide a successful therapy for clinical use of a broad range of patients, oral administration of active agent is one of the favourite routes of administration due to high patient compliance.

Therefore, it is an object of the present invention to provide an oral dosage form suitable to provide high plasma concentration levels of hydroxynorketamine to be used in the treatment of depression.

The inventors of the present invention have surprisingly found that oral administration of at least one prodrug of hydroxynorketamine in a modified-release dosage form results in very advantageous in vivo pharmacokinetic properties of hydroxynorketamine.

Hence, one aspect of the present invention relates to hydroxynorketamine for use in the treatment of depression, wherein hydroxynorketamine is administered in form of at least one prodrug, and wherein the at least one prodrug is orally administered in a modified-release dosage form.

This first aspect of the present invention also refers to a method of treating depression comprising administering hydroxynorketamine in form of at least one prodrug, wherein the at least one prodrug is orally administered in a modified-release dosage form.

In addition, the first aspect of the present invention concerns the use of hydroxynorketamine in the manufacturing of a medicament for the treatment of depression, wherein hydroxynorketamine is in the form of at least one prodrug, and wherein the medicament is a modified-release dosage form for oral administration.

A second aspect of the present invention relates to an oral modified-release dosage form for use in the treatment of depression, wherein the oral modified-release dosage form comprises at least one prodrug of hydroxynorketamine.

The second aspect of the present invention also refers to a method of treating depression comprising administering an oral modified-release dosage form, wherein the oral modified-release dosage form comprises at least one prodrug of hydroxynorketamine.

In addition, the second aspect of the present invention concerns the use of at least one prodrug of hydroxynorketamine in the manufacturing of a medicament for the treatment of depression, wherein the medicament is an oral modified-release dosage form.

The following definition of terms and description of embodiments applies for both aspects of the invention. Further, the first aspect and the second aspect of the invention are not mutually exclusive, i.e. embodiments of the first aspect can at the same time comprise the features of the second aspect and vice versa.

The term "depression" as used herein is understood to encompass major depressive disorder and bipolar depression.

In one embodiment of the invention, the treatment of depression is a long-term treatment. In a preferred embodiment the long-term treatment last for at least one month, preferably at least two months and more preferably at least three months.

The term "prodrug" according to the present invention means any compound that is metabolized to hydroxynorketamine when orally administered to a mammalian subject.

In a preferred embodiment the at least one prodrug is selected from (S)-Ketamine, (R)-Ketamine, (R,S)-Ketamine. (S)-Norketamine, (R)-Norketamine, (R,S)-Norketamine, (S)-Hydroxyketamine, (R)-Hydroxyketamine, (R,S)-Hydroxyketamine or pharmaceutically salts or solvates or mixtures thereof. In a more preferred embodiment the at least one prodrug is (R,S)-Ketamine or a pharmaceutically salt or solvate thereof.

The metabolic pathway of ketamine shown in the following is derived from Zarate et al., Relationship of Ketamine's Plasma Metabolites with Response, Diagnosis, and Sife Effects in Major Depression, 2012, Biol. Psychiatry, 72(4): 331-338) (Ket, ketamine; HK, hydroxyketamine; HNK, hydoxynorketamine; DHNK, dehydronorketamine):

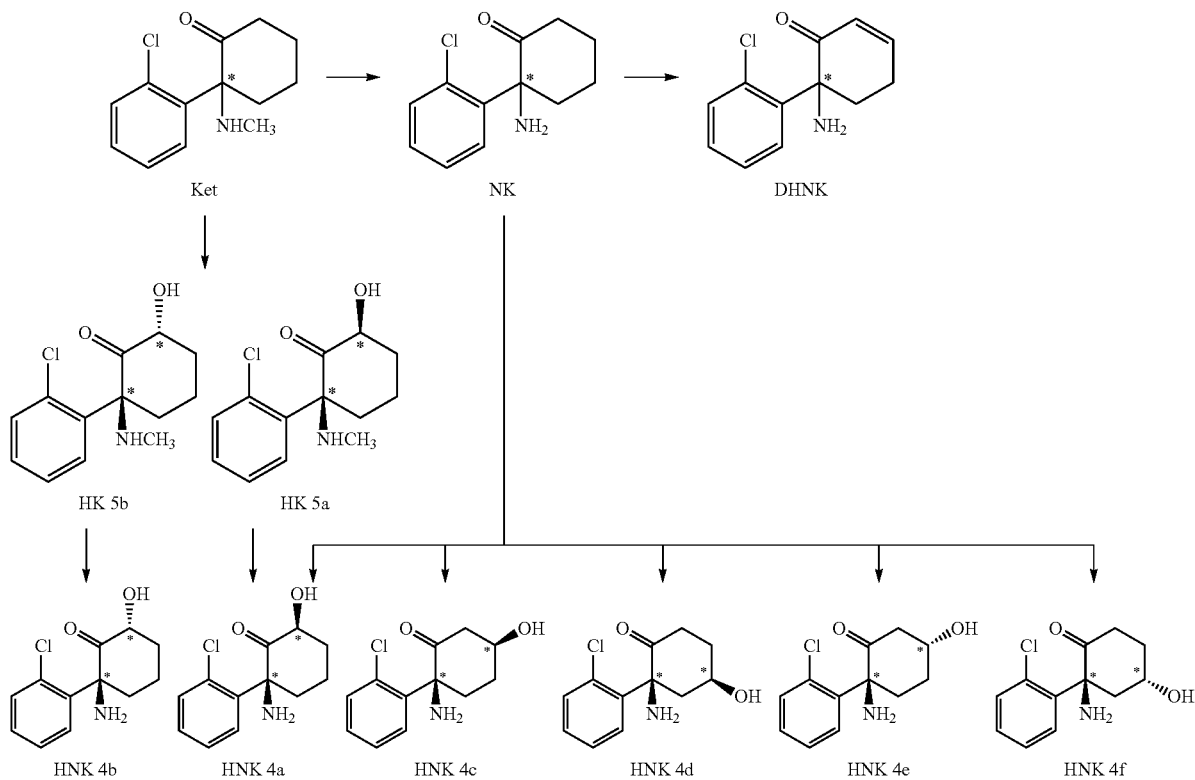

The term "modified-release dosage form" relates to a solid single-dose preparation for oral administration showing a rate, a place and/or a time of release different from that of a conventional dosage form, e.g. an immediate-release dosage form.

In one embodiment of the invention the modified-release dosage form is selected from prolonged-release, delayed-release and pulsatile-release dosage form. In a preferred embodiment the modified-release dosage form is a prolonged-release dosage form.

In one preferred embodiment of the invention the prolonged-release dosage form comprises (R,S)-ketamine, preferably (R,S)-ketamine hydrochloride. It has been found that administration of (R,S)-ketamine hydrochloride as a prodrug for hydroxynorketamine in an oral prolonged-release dosage form generates surprisingly much higher plasma concentration levels of hydroxynorketamine compared to intravenous and oral administered ketamine in an immediate-release dosage form. In particular, it was found that administration of (R,S)-ketamine in a prolonged-release dosage form according to the present invention results in a ratio of $AUC_{K/HNK}$ between 1:7 and 1:20 depending on the dose. In contrast, intravenous administration of (R,S)-ketamine merely led to a $AUC_{K/HNK}$ of 1:0.3. Beyond that, from the Rao et al., 2016, it is known that immediate oral administration (R,S)-Ketamine results in a $AUC_{K/HNK}$ between 1:3.8 and 1:5 (Rao et al., Role of Cytochrome P4502B6 Polymorphisms in Ketamine Metabolism and Clearance, Anesthesiology, 2016, V 125, No. 6, p. 1103-1112). In addition, the plasma concentration levels of (R,S)-ketamine administered with the prolonged-release dosage of the invention are such low that the usual ketamine-induced side effects, such as dizziness, abuse liability etc., are avoided.

These plasma concentration levels show that administration of (R,S)-ketamine in a prolonged-release dosage form according to the present invention allows significant metabolization of (R,S)-ketamine into hydroxynorketamine required for the treatment of depression.

In a particular preferred embodiment of the present invention oral administration of the prolonged-release dosage form comprising (R,S)-ketamine hydrochloride results in plasma concentration profiles exhibiting a ratio of $AUC_{K/HNK}$ between 1:7 and 1:25 and preferably 1:14 and 1:20. Optionally, the ratio of $AUC_{K/NK}$ is between 1:10 and 1:25, preferably between 1:10 and 1:22 and most preferably 1:14 and 1:22.

In one embodiment of the invention the prolonged-release dosage form is selected from a diffusion-controlled release system, a dissolution-controlled release system, an erosion-controlled release system or an osmosis-controlled release system, preferably a diffusion-controlled release.

In a diffusion-controlled prolonged-release system the transport by diffusion of dissolved active agents in pores filled with gastric or intestinal juice or in a solid phase is the release-controlling step.

Diffusion-controlled prolonged-release systems can be matrix systems (also known as monolithic systems) and reservoir systems.

In one embodiment of the invention, the diffusion-controlled prolonged-release dosage form is in the form of a reservoir system. A reservoir system according to the present invention comprises a release unit in form of a tablet or a nearly spherical particle of about 200 to 1000 µm diameter.

The at least one prodrug of hydroxynorketamine can be dissolved or dispersed in the reservoir system. The release unit of the reservoir system is surrounded by a membrane through which diffusion takes place. Therefore, the reservoir system of the present invention comprises a release unit surrounded by a membrane. The membrane is usually formed by high molecular weight polymers, such as cellulose derivate or acrylates, preferably ethyl cellulose. The membrane preferably comprises water-soluble polymers, such as hydroxypropylmethylcellulose and/or hydroxypropylcellulose. In such a membrane the water-soluble component will dissolve and form pores filled with liquid through which the active agent can diffuse. The membrane optionally may comprise a plasticizer. The reservoir system of the present invention can be designed as multiple-unit or single unit system, preferably as multiple unit system.

In another embodiment of the invention, the prolonged-release dosage form is in the form of a matrix system. A matrix system can be either a diffusion-controlled or a erosion-controlled release system. Therefore, the matrix system of the present invention is preferably swellable, non-swellable, erodible or non-erodible, and preferably comprises polymers, including synthetic polymers, and naturally occurring polymers and derivatives, such as polysaccharides and proteins. In a further embodiment, the matrix system is a non-crodible matrix system. The at least one prodrug of hydroxynorketamine can be dissolved or dispersed in an inert matrix system and thereby, and is released by diffusion through the inert matrix once administered.

Preferred materials for forming a matrix system comprise chitin, chitosan, dextran, and pullulan, gum agar, gum arabic, gum karaya, locust bean gum, gum tragacanth, carrageenans, gum ghatti, guar gum, xanthan gum, and scleroglucan, starches, such as dextrin and maltodextrin, hydrophilic colloids, such as pectin, phosphatides, such as lecithin, alginates, propylene glycol alginate, gelatin, collagen, and cellulosics, such as ethyl cellulose (EC), methylethyl cellulose (MEC), carboxymethyl cellulose (CMC), carboxymethyl ethylcellulose (CMEC), hydroxyethyl cellulose (HEC), hydroxypropyl cellulose (HPC), cellulose acetate (CA), cellulose propionate (CP), cellulose butyrate (CB), cellulose acetate butyrate (CAB), cellulose acetate phthalate (CAP), cellulose acetate trimellitate (CAT), hydroxypropyl methyl cellulose (HPMC), HPMCP, HPMCAS, hydroxypropyl methyl cellulose acetate trimellitate (HPMCAT), and ethylhydroxy ethylcellulose (EHEC), polyvinyl pyrrolidone, polyvinyl alcohol, polyvinyl acetate, fatty acid esters, polyacrylamide, polyacrylic acid, copolymers of ethacrylic acid or methacrylic acid (EUDRAGIT), Rohm America, Inc., Piscataway, NJ), poly(2-hydroxyethylmethacrylate), polylactides, copolymers of L-glutamic acid and ethyl-L-glutamate, degradable lactic acid-glycolic acid copolymers, poly-D-(-)-3-hydroxybutyric acid, and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

The matrix forming material is preferably present in the prolonged-release dosage form of the invention in a concentration of between 10 and 95 wt.-%, more preferably 20 to 75%, in particular 25 to 65%, based on the total weight of the dosage form.

The prolonged-release dosage form comprising a matrix system may further comprise excipients such as lubricants, fillers, glidants, binders, stabilizers. Regarding preferred embodiments of said excipients it is referred to explanations given below.

In a preferred embodiment the prolonged-release dosage form comprises 10 and 95 wt.-%, more preferably 20 to 75%, in particular 30 to 65% matrix forming material, 0 to 90 wt.-%, preferably 5 to 70 wt. %, more preferably 10 to 50 wt. %, in particular 15 to 30 wt.-% fillers, optionally 0 to 25 wt.-%, preferably 1 to 20 wt. %, more preferably 5 to 15% binders, 0 to 5 wt.-%, preferably 0.1 to 4 wt. %, more preferably 0.5 to 3% glidants, 0 to 5 wt.-%, preferably 0.1 to 3 wt. %, more preferably 0.3 to 2% lubricants based on the total weight of the dosage form.

The matrix system of the prolonged-release dosage form can be prepared by direct-compression, wet-granulation or dry-granulation. Direct compression is a preferred embodiment. For more detailed explanations about the compression step it is referred to the illustrations given below.

In a further embodiment of the invention, the prolonged-release dosage form can be present in form of an osmosis-controlled release system, including one-chamber system (elementary osmotic pump), two-chamber system (push-pull systems), asymmetric membrane technology (AMT), and extruding core system (ECS). Osmosis-controlled release system should comprise cores, for example tablets, comprising a prodrug of hydroxynorketamine, which are enveloped by a semipermeable membrane which preferably has at least one orifice. The water-permeable membrane is impermeable to the components of the core but permits water to enter the system from outside by osmosis. The water which penetrates in then, through the osmotic pressure produced, releases the active ingredient in dissolved or suspended form from the orifice(s) in the membrane. The total active ingredient release and the release rate can substantially be controlled via the thickness and porosity of the semipermeable membrane, the composition of the core and the number and size of the orifice(s).

In addition to the at least one prodrug of hydroxynorketamine, the core of the osmotic device optionally includes an osmotic agent which preferably creates a driving force for transport of water from the environment of use into the core of the device.

In the osmotic two-chamber system, the core consists of two layers, one active ingredient layer and one osmosis layer. The active ingredient layer preferably comprises 1 to 70% ketamine, 30 to 95% of one or more osmopolymers. The osmosis layer preferably comprises 30 to 90% of one or more osmopolymers, 10 to 60% of an osmogen, where the difference from 100% in the individual layers is formed in each case independently of one another by one or more additional ingredients in the form of pharmaceutically usual excipients. The osmogens and osmopolymers used in the core of the osmotic two-chamber system may be as described in the following paragraphs.

In one embodiment, the osmotic agents are water-swellable polymers, which are also referred to as "osmopolymers" and "hydrogels," including hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

In a second embodiment, the osmotic agents are osmogens which are capable of imbibing water to affect an osmotic pressure gradient across the barrier of the surrounding coating. Preferred osmogens comprise water-soluble salts of inorganic or organic acids or nonionic organic substances with a high solubility in water, such as for example carbohydrates, especially sugars, sugar alcohols or amino acids. For example, the osmogens are selected from inorganic salts such as chlorides, sulphates, carbonates and bicarbonates of alkali metals or alkaline earth metals, such as lithium, sodium, potassium, magnesium, calcium, and phosphates, hydrogen phosphates or dihydrogen phosphates, acetates, succinates, benzoates, citrates or ascorbates thereof. It is furthermore possible to use pentoses such as arabinose, ribose or xylose, hexoses such as glucose, fructose, galactose or mannose, disaccharides such as sucrose, maltose or lactose or trisaccharides such as raffinose. The water-soluble amino acids include glycine, leucine, alanine or methionine. Sodium chloride is particularly preferably used according to the invention. The osmogens are preferably present in an amount of 10 to 30% based on the total mass of the core ingredients.

In one embodiment, a combination of osmogens and osmopolymers is used in the osmosis-controlled release system.

The core further comprises pharmaceutically acceptable excipients comprising buffer substances such as sodium bicarbonate, binders such as hydroxypropylcellulose, hydroxypropylmethylcellulose and/or polyvinylpyrrolidone, lubricants such as magnesium stearate, wetting agents such as sodiumlauryl sulphate and/or flow regulators such as colloidal silicon dioxide.

Materials for forming the semipermeable membrane of the osmosis-controlled release system include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Preferably, the material for forming the semipermeable membrane comprises plasticized, unplasticized, and reinforced cellulose acetate (CA), cellulose diacetate, cellulose triacetate. CA propionate, cellulose nitrate, cellulose acetate butyrate (CAB), CA ethyl carbamate, CA phthalate, CA methyl carbamate. CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylenevinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural and synthetic waxes.

In a further embodiment, the semipermeable membrane may also be a hydrophobic microporous membrane which is permeable to water vapor, as disclosed in U.S. Pat. No. 5,798,119. Hydrophobic polymers for forming hydrophobic but water-permeable membranes comprise polyalkenes, polyethylene, polypropylene, polytetrafluoro-ethylene, polyacrylic acid derivatives, polyethers, polysulfones, polyethersulfones, polystyrenes, polyvinyl halides, polyvinylidene fluoride, polyvinyl esters and ethers, natural and synthetic waxes.

The delivery port(s) on the semipermeable membrane are formed post-coating by mechanical or laser drilling. Alternatively, delivery port(s) are formed in situ by erosion of a plug of water-soluble material or by rupture of a thinner portion of the membrane over an indentation in the core. Yet further, delivery ports are formed during the coating process, as in the case of asymmetric membrane coatings.

The osmosis-controlled release dosage form can be prepared according to conventional methods and techniques known to those skilled in the art (see Santus and Baker, J Controlled Release 1995, 35, 1-21; Verma et al., Drug Development and Industrial Pharmacy 2000, 26, 695-708; Verma et al., J Controlled Release 2002, 79, 7-27).

As described above, the dosage form disclosed herein can be an AMT controlled release dosage form, which comprises an asymmetric osmotic membrane that coats a core comprising ketamine and other pharmaceutically acceptable excipients or carriers. (See U.S. Pat. No. 5,612,059 and WO 2002/17918). The AMT controlled release dosage forms can be prepared according to conventional methods and techniques known to those skilled in the art, including direct compression, dry granulation, wet granulation, and a dip-coating method.

In further embodiments, the modified-release dosage form disclosed herein is formulated as ECS prolonged-release dosage form, which comprises an osmotic membrane that coats a core comprising a prodrug of hydroxynorketamine, hydroxyethyl cellulose, and other pharmaceutically acceptable excipients or carriers.

In one embodiment of the invention the modified-release dosage form is a single-unit or a multiple-unit dosage form.

In a preferred embodiment of the invention, the prolonged-release dosage form is in the form a diffusion-controlled release system comprising a multitude of particles. Particles may be pellets, granules, spheroids, microtablets. Preferably, particles are pellets which contain a core comprising a prodrug of hydroxynorketamine or a pharmaceutically acceptable salt or solvate thereof.

Preferably, the pellets contain a core comprising at least one prodrug of hydroxynorketamine and a prolonged-release control layer in form of a membrane coated upon the core. Preferably, the prolonged-release control layer is applied over the prodrug of hydroxynorketamine containing core. The at least one prodrug of hydroxynorketamine containing core may be a core which contains at least one prodrug of hydroxynorketamine and excipients. In those embodiments, the excipients preferably do not substantially retard or delay the release of the at least one prodrug of hydroxynorketamine.

Preferably, the core comprises a layer of at least one prodrug of hydroxynorketamine on an inert core. The inert core (also referred to as seed core or neutral bead) may be granules or beads, preferably spherical, and further preferably made from sugar or cellulose or other suitable materials. By way of example, spherical inert cores based on saccharose, such as those commercially available under the trade name Suglets® or those based on cellulose, such as those commercially available under the trade name Celphere® or Cellets® may be mentioned. Saccharose-based inert cores are particularly preferred. Inert cores may preferably have a particle size in the range of 100 to 500 μm and more preferably in the range of 200 to 400 μm, with the particle size range indicating the size range for 90% of the particles as determined by sieve analysis.

Preferably, the at least one prodrug of hydroxynorketamine is provided by coating at least one prodrug of hydroxynorketamine-containing layer directly onto the inert cores. The at least one prodrug of hydroxynorketamine-containing layer preferably does not sustain or delay release of at least one prodrug of hydroxynorketamine, i.e. is an immediate-release layer.

In one embodiment, each pellet contains a core comprising at least one prodrug of hydroxynorketamine and a release control layer coated upon the core. In an alternative embodiment, pellets containing the prodrug of hydroxynorketamine cores and a release control layer coated upon the cores can be mixed to other pellets.

In an embodiment of the invention, the core does not comprise a neutral bead as described above, but a bead comprising at least one prodrug of hydroxynorketamine and optionally at least one pharmaceutically acceptable excipient. The at least one prodrug of hydroxynorketamine containing bead can be formed by dry granulation, wet granulation, spray granulation or extrusion.

Preferably, a suitable at least one prodrug of hydroxynorketamine-containing core comprises 10 to 50 wt. %, preferably 15 to 40 wt. %, more preferably 20 to 30 wt. % inert core (neutral bead), 20 to 90 wt. %, preferably 35 to 80 wt. %, more preferably 50 to 70 wt. % of at least one prodrug of hydroxynorketamine, in particular (R,S) ketamine hydrochloride, 0.1 to 20 wt. %, preferably 1 to 15 wt. %, more preferably 3 to 10 wt. % binder, and optionally 0 to 20 wt. %, preferably 1 to 15 wt. %, more preferably 3 to 10 wt. % glidant, based on the total weight of the at least one prodrug of hydroxynorketamine-containing core.

Binders generally serve to enhance the integrity and stability of tablets. In addition, they may improve the suitability of pharmaceutical compositions for granulation. Binders are commonly also used for the preparation of films and for the preparation of active agent containing layers, around an inert core. Exemplary binders include synthetic polymers, such as polyvinyl pyrrolidone (PVP), vinyl pyrrolidone-vinyl acetate-copolymer, modified celluloses, such as hydroxy alkyl celluloses and mixtures thereof. A binder is typically used in an amount of 0 to 25% by weight, preferably 0.1 to 15% by weight and in further embodiments 1 to 10% by weight of the controlled release oral dosage form. Preferably, hypromellose (HPMC) or PVP is used as binder in the hydroxynorketamine-prodrug-containing core, more preferably HPMC. Preferably, said HPMC has a methoxy content of 20% to 40%, more preferably 25% to 35%. Further, preferably said HPMC has a hydroxypropoxy content of about 5% to 15%, more preferably 7% to 12%. Preferably, a 2% by weight (aqueous) solution of said HPMC has a viscosity of 0.5 to 100 mPa·s, preferably 1 to 50 mPa·s, more preferably 2 to 10 mPa-s, measured at 20° C., preferably by means of a Brookfield-Synchro-Lectric LVF viscosimeter. Preferably, the PVP has an average molecular weight of 1,000 to 2,500,000, preferably 5,000 to 2,000.000, more preferably 10,000 to 1,500,000.

Generally, glidants such as disperse silica, such as Aerosil®, or talc can be used. In particular, talc is used as glidant in the at least one prodrug of hydroxynorketamine-containing core.

In one embodiment, the at least one prodrug of hydroxynorketamine-containing core does not comprise a glidant.

The prolonged-release control layer in form of a membrane may be disposed in direct vicinity, i.e. in immediate contact with and surrounding the hydroxynorketamine prodrug—containing core, which is preferred. In other exemplary embodiments, an intermediate layer may be disposed between the at least one prodrug of hydroxynorketamine-containing core and the prolonged-release control layer. This intermediate layer may further control the release of the at least one prodrug of hydroxynorketamine-containing from the core. However, it is preferred that, if present, the intermediate layer does not substantially influence the release from the core.

The prolonged-release control layer comprises a release control substance for controlling the release of the at least one prodrug of hydroxynorketamine-containing from the pellets. The release control substance may be any substance known in the art as suitable to control the release of an active substance. Exemplary embodiments of suitable control release substances include cellulose esters, such as cellulose acetate phthalate, polyvinyl pyrrolidone, polyvinyl alcohol, polyvinyl acetate, polyvinyl chloride, nylon, polyamide, polyethylene oxide, polylactide-co-glycolide and mixtures thereof. Further suitable polymers include those selected from alkylcelluloses, in particular cellulose ethers, polymers and copolymers based on acrylate or methacrylate, polymers and copolymers based on acrylic or methacrylic esters and mixtures thereof. Preferably, the release control substance is a water insoluble polymer, preferably an alkyl cellulose. More preferably, the alkyl cellulose is ethyl cellulose.

In exemplary embodiments of the present invention wherein the release control substance is a polymer, said polymer has a weight average molecular weight of 5,000 to 500,0000 g/mol, preferably of 50.000 to 900,000 g/mol, more preferably of 100,000 to 400,000 g/mol, for instance of 140.000 to 300,000 g/mol. The weight average molecular weight is preferably determined by gel permeation chromatography.

In further embodiments, and in addition or in the alternative to one or more of the properties mentioned above, the release control substance, and in particular the polymer, preferably has a solubility in water of less than 20 mg/l, preferably less than 15 mg/l, preferably between 0.001 to 10.0 mg/l. The solubility in water is preferably determined in accordance with European Regulation RL67-548 EWG, Annex V, Chapter A6 (German version referred to and referenced herein).

In further embodiments where a polymer is used as or as part of the release control substance, and in addition or in the alternative to one or more of the properties mentioned above, the polymer has a glass transition temperature of 20 to 220° C., for instance 60 to 150° C. or 90 to 140° C. The glass transition temperature is preferably measured by means of differential scanning calorimetry DSC, preferably using a Mettler Toledo instrument and a preferably applying a heating/cooling rate of 10° C. per minute.

In a particularly preferred embodiment the prolonged-release control substance is ethylcellulose having an ethoxyl content of about 30 to 70%, more preferred of about 40 to 60%. Preferably, a 2% by weight (aqueous) solution of ethylcellulose has a viscosity of 5 to 500 mPa·s, preferably 10 to 100 mPa·s, measured at 25° C., preferably by means of a Brookfield-Synchro-Lectric LVF viscosimeter.

In exemplary embodiments, the prolonged-release control substance is contained in an amount of 0.1 to 80% by weight of the total weight of the pellets in the dosage form, more preferably in amounts of 0.5 to 60% by weight, 10 to 50% by weight, 15 to 40% by weight, of the total weight of the pellets in the dosage form.

Control of the prolonged release rate can be adapted by appropriate selection of the control release substance or mixture of such substances, its/their amount, coating thickness, inclusion of further excipients, such as pore formers and/or plasticizers or others.

Further to the prolonged-release control substance, one or more additional excipients may be used, in particular in a release control layer. A preferred excipient for use with the release control substance, in particular a polymeric release control substance, is a plasticizer and/or a pore builder and/or glidants.

A plasticizer, as the term is used herein, is a substance that typically lowers the glass transition temperature of the polymer it is used in admixture with by at least 2° C., preferably at least 5° C., for instance between 5 and 30° C., as compared to the polymer alone. Preferably, the plasticizer is triethyl citrate or propylene glycol.

A pore former usually is a substance having a water-solubility which is higher than the water solubility of the release-control substance. Preferably, the pore former has a solubility in water of more than 20 mg/l, preferably 50 mg/l to 5000 mg/l, more preferably 100 to 1000 mg/l. The solubility in water is preferably determined as described above. In particular, hydroxypropyl cellulose (HPC) is used as pore former.

In a preferred embodiment, the prolonged-release control layer comprises 20 to 95 wt. %, preferably 40 to 80 wt. %, more preferably 50 to 70 wt. % release control substance, preferably as described above, 0.1 to 30 wt. %, preferably 1 to 25 wt. %, more preferably 5 to 20 wt. % pore builder, preferably as described above, 0.1 to 30 wt. %, preferably 1 to 25 wt. %, more preferably 5 to 20 wt. % plasticizer, preferably as described above, and optionally 0 to 40 wt. %, preferably 3 to 30 wt. %, more preferably 5 to 20 wt. % glidant, preferably as described above, based on the total weight of the release control layer.

The prolonged-release control layer may be a single layer or a plurality of layers. For ease of fabrication, embodiments with a single release control layer are preferred.

The pellets may be used as a pharmaceutical formulation, for instance, without any further processing. For this kind of administration, the pellets are preferably filled into sachets. In the alternative, they may be incorporated into capsules, optionally together with one or more excipients, or into other suitable ingestible pharmaceutical dosage forms.

Most preferably, the pellets are contained in an external phase of at least one pharmaceutically acceptable excipient. Furthermore, the prolonged-release oral dosage form is a tablet or a capsule, and preferably a tablet.

As evident from what has been set out before, most preferably, the oral dosage form according to the present invention does not contain the at least one prodrug of hydroxynorketamine in an immediate-release form, i.e. does not contain the at least one prodrug of hydroxynorketamine, the release of which is not prolonged.

In particularly preferred embodiments, the pellets are mixed to a so-called "external phase" in order to be compressed into tablets. The external phase should ensure the stability of the pellets during the compression and is usually composed of one or more pharmaceutically acceptable excipients, such as fillers, binders, disintegrants, glidants and lubricants.

Fillers are normally used to dilute a pharmaceutical composition and provide bulk. Examples for preferred fillers include lactose, starch, calcium phosphate, calcium carbonate, saccharose, sugar alcohols such as mannitol, sorbitol, xylitol, and celluloses and derivatives. Microcrystalline cellulose is particularly preferred.

In a preferred embodiment a filler mixture comprising sodium carboxymethyl cellulose and microcrystalline cellulose, preferably in a weight ratio of 5:1 to 1:5, more preferably 3:1 to 1:3 is used. A filler or mixture of fillers may be used in an amount of 0 to 80% by weight, preferably 1 to 70% by weight, based on the total weight of the controlled release oral dosage form, preferably the tablet.

Binders generally serve to enhance the integrity and stability of tablets. In addition, they may improve the suitability of pharmaceutical compositions for granulation. Binders are commonly also used for the preparation of films, such as active agent containing layers, around an inert core. Exemplary binders include synthetic polymers, such as polyvinyl pyrrolidone, modified celluloses, such as hydroxy alkyl celluloses and mixtures thereof. A binder is typically used in an amount of 0 to 30% by weight, preferably 0.1 to 15% by weight and in further embodiments 1 to 10% by weight of the controlled release oral dosage form. Preferably hypromellose (HPMC) is used as binder.

A disintegrant enhances the disintegration of a dosage form, in particular a tablet, after its immersion in water or gastric juices. Suitable disintegrants include carrageenan, starchs, croscarmellose, crospovidone and mixtures thereof. Disintegrants may be used in amounts of 0 to 25% by weight, preferably 1 to 20% by weight and in further embodiments 3 to 15% by weight of the controlled release oral dosage form, preferably the tablet.

The prolonged-release dosage forms may further include a glidant, such as disperse silica, such as Aerosil®, or talc. A glidant (or mixture thereof) may be comprised in an amount of 0 to 5% by weight, for instance 0.1 to 4% by weight of the prolonged-release oral dosage form, preferably the tablet.

The prolonged-release dosage form may further comprise a lubricant, in particular in tablets prepared by compression. Suitable lubricants include stearic acid, magnesium stearate, adipic acid and sodium stearyl fumarate (Pruv®).

Preferably, the amount of pellets in the prolonged-release dosage form ranges from 1% to 100% by weight, based on the total weight of the prolonged-release dosage form. In preferred embodiments, the pellets are comprised in an amount of 20% to 90% by weight, more preferably 25% to 80% by weight, based on the total weight of the prolonged-release dosage form.

In a preferred embodiment the external phase (without coated cores) comprises 85 to 99.9%, preferably 90 to 98% by weight filler, 0 to 5%, preferably 0.1 to 1.0% by weight lubricant and 0.1 to 10%, preferably 1.0 to 5% by weight glidant, based on the total weight of the external phase.

Optionally, the prolonged-release dosage form, particularly when present in the form of a tablet, can comprise an external film for improved ease of swallowing, for protection, for colouring, for taste-masking or other purposes. Preferably, this external film does not influence the release of hydroxynorketamine prodrug to any significant extent. The external film may comprise the usual excipients known in this art for this purpose. A combination of hypromellose, talc, a colouring agent, such as titanium dioxide, and/or a polymer, such as polyethylene glycol is a preferred embodiment herein. Preferably, ready to use products like Opadry®, based on hypromellose or polyvinyl alcohol are used for the film coating. This optional film is not counted towards the total weight of the controlled release oral dosage form herein. Expressed differently, any amount of an ingredient expressed as weight percent herein refers to the controlled release oral dosage form without this optional external film. As evident from the above, the external film is free of hydroxynorketamine prodrug in any form.

The prolonged-release dosage form has the advantage that it may be divided into two or more units without impairing the controlled release of the at least one prodrug of hydroxynorketamine. The prolonged-release dosage form, and in particular the tablet, may therefore comprise means facilitating its division into two or more units, such as a break-line, each of said units providing prolonged-release of the at least one prodrug of hydroxynorketamine. The dosage form therefore provides for the possibility to adjust the dosage, for instance halve the dosage by breaking the tablet in two.

In preferred embodiments according to the present invention, the at least one prodrug of hydroxynorketamine is a ketamine, preferably, (R,S) ketamine or (R,S) ketamine hydrochloride. The dosage form may contain ketamine in amounts of 5 to 400 mg, preferably 5 to 200 mg. If ketamine is used as free base, the amount of 5 to 400 mg refers to the weight of the free base. If ketamine is used in the form of a pharmaceutical acceptable salt, the amount of 5 to 400 mg refers to the weight of the salt. Preferably, the dosage form of the present invention comprises 10 mg ketamine, 20 mg ketamine, 40 mg ketamine, 80 mg ketamine, 100 mg ketamine, 120 mg ketamine, 140 mg ketamine, 160 mg ketamine, 180 mg ketamine, 200 mg ketamine, 220 mg ketamine, 240 mg ketamine, 260 mg ketamine, 280 mg ketamine, 300 mg ketamine, 320 mg ketamine, 340 mg ketamine, 360 mg ketamine, 380 mg ketamine, more preferably 10 mg ketamine hydrochloride, 20 mg ketamine hydrochloride, 40 mg ketamine hydrochloride, 80 mg ketamine hydrochloride, 100 mg ketamine hydrochloride, 120 mg ketamine hydrochloride, 140 mg ketamine hydrochloride, 160 mg ketamine hydrochloride, 180 mg ketamine hydrochloride, 200 mg ketamine hydrochloride, 220 mg ketamine hydrochloride, 240 mg ketamine hydrochloride, 260 mg ketamine hydrochloride, 280 mg ketamine hydrochloride, 300 mg ketamine hydrochloride, 320 mg ketamine hydrochloride, 340 mg ketamine hydrochloride, 360 mg ketamine hydrochloride, 380 mg ketamine hydrochloride.

It is preferred that the prolonged-release dosage form of the present invention comprises:

i) ketamine-containing cores comprising 1 to 30 wt. %, preferably 2 to 20 wt. %, more preferably 3 to 10 wt. % inert cores, 1 to 40 wt. %, preferably 5 to 20 wt. %, more preferably 10 to 15 wt. % ketamine, in particular ketamine hydrochloride, 0.01 to 10 wt. %, preferably 0.1 to 5 wt. %, more preferably 0.5 to 3 wt. % binder, and 0 to 10 wt. %, preferably 0.1 to 5 wt. %, more preferably 0.5 to 3 wt. % glidant, ii) a release-control layer coated on each ketamine-containing core, comprising 1 to 40 wt. %, preferably 3 to 20 wt. %, more preferably 7 to 15 wt. % release-control substance, 0.01 to 10 wt. %, preferably 0.1 to 6 wt. %, more preferably 1 to 4 wt. % pore builder, 0 to 10 wt. %, preferably 0.1 to 6 wt. %, more preferably 1 to 4 wt. % plasticizer, 0 to 15 wt. %, preferably 0.1 to 10 wt. %, more preferably 0.5 to 5 wt. % glidant, and iii) an external phase comprising 20 to 85%, preferably 40 to 75%, more preferably 50 to 65% filler, 0 to 3 wt. %, preferably 0.001 to 2.0 wt. %, more preferably 0.1 to 0.5 wt. % lubricant and 0 to 5 wt. %, preferably 0.1 to 5 wt. %, more preferably 0.5 to 2.0 wt. % glidant, wherein all wt. % are based on the total weight of the tablet (without film coating).

The tablets of the present invention preferably have a tablet height of 2 to 8 mm, more preferably 3 to 5 mm, and a length of 3 to 22 mm, preferably 5 to 17 mm. Preferably, the tablets have a hardness of 40 to 300 N, more preferably of 50 to 200 N.

In a further embodiment of the invention, the administration of a single oral dosage form leads in-vivo to a $C_{max}$ of ketamine of 1 to 150 ng/ml, preferably 2 to 120 ng/ml, more preferably 3 to 100 ng/ml, still more preferably 4 to 70 ng/ml, further more preferably 5 to 40 ng/ml, and to a $AUC_{0-\infty}$ of 5 to 1000 ng·h/ml, preferably 10 to 750 ng·h/ml, more preferably 50 to 600 ng·h/ml, still more preferably 100 to 400 ng·h/ml.

In a further embodiment, the administration of a single oral dosage form leads in-vivo to a $C_{max}$ of norketamine of 5 to 750 ng/ml, preferably 10 to 600 ng/ml, more preferably 15 to 500 ng/ml, still more preferably 20 to 400 ng/ml, further more preferably 25 to 300 ng/ml, and to a $AUC_{0-\infty}$ of 100 to 8000 ng·h/ml, preferably 150 to 6000 ng·h/ml, more preferably 500 to 4000 ng·h/ml.

"$C_{max}$" means the peak concentration of ketamine in the plasma, e.g. determined as described below. "$AUC_{0-\infty}$" describes ketamine bioavailability and is measured by calculating the area under curve (AUC) of the plasma drug concentration time profile from time zero extrapolated to infinity.

In a further preferred embodiment of the invention, $T_{max}$ of ketamine is 3 to 9 h, preferably 3 to 8 h, more preferably 4 to 7 h, most preferably 5 to 7 h.

In a further preferred embodiment of the invention, $T_{max}$ of norketamine is 3 to 9 h, preferably 3 to 8 h, more preferably 4 to 7 h, most preferably 5 to 7 h.

"$T_{max}$" means the time from administration to reach $C_{max}$.

In a further preferred embodiment of the invention, the oral prolonged-release dosage form has a $F_{abs}$ of 5 to 25%, preferably 7 to 20%, more preferably 9 to 18%.

"$F_{abs}$" is the absolute bioavailability. Absolute bioavailability compares the bioavailability of the active drug in systemic circulation following non-intravenous administration (i.e., after oral administration in the present case), with the bioavailability of the same drug following intravenous administration. It is the fraction of the drug absorbed through non-intravenous administration compared with the corresponding intravenous administration of the same drug. The absolute bioavailability is the dose-corrected area under curve (AUC) non-intravenous (oral) divided by AUC intravenous. For example, the formula for calculating $F_{abs}$ for a drug administered by the oral route is given below:

$$F_{abs} = AUC_{oral}/AUC_{iv} \times dose_{iv}/dose_{oral}$$

The oral prolonged-release dosage form of the present invention is administered once or twice daily, preferably twice daily.

The invention will be further described by way of exemplary embodiments.

EXAMPLES

Example 1: Preparation of Matrix Controlled Release Tablets Containing 20 mg Ketamine Hydrochloride

| | |
|---|---|
| Ketamine HCl | 20.00 mg |
| Kollidon ® SR | 78.50 mg |

| | |
|---|---:|
| Aerosil 200 | 1.00 mg |
| Magnesium stearate | 0.50 mg |
| Total tablet | 100.00 mg |

Ketamine HCl, Kollidon® SR and Aerosil 200 are sieved through a 630 μm sieve and mixed for 15 minutes.

Magnesium stearate is added to the mixture and further mixed for 2 minutes. Tablets with the composition outlined in the table above are pressed on a rotary machine with oblong punches 9*4 mm.

Example 2: Preparation of Capsules Containing 20 mg Ketamine Hydrochloride

Step 1:

A spraying solution is prepared from the following ingredients:

| | |
|---|---:|
| Hypromellose | 22.5 g |
| Ketamine hydrochloride | 150.0 g |
| Ethanol 96% | q.s. |
| Water, purified | q.s. |

A spraying suspension is prepared by successively dissolving hypromellose and ketamine hydrochloride in a mixture of purified water and ethanol [1:2.75 m/m].

60.0 g sugar spheres (saccharose, particle size range (90%) 200 to 400 μm) are filled into a fluid-bed processor with a bottom-spray nozzle and pre-heated. The spraying suspension is then sprayed onto the sugar spheres in the fluid-bed processor, thus preparing a plurality of sugar spheres having a layer of ketamine coated thereupon. The coated sugar spheres are then sieved to remove agglomerates (vibration sieve or equivalent).

Step 2:

A coating suspension is prepared from the following ingredients:

| | |
|---|---:|
| Ethylcellulose | 54.0 g |
| Hydroxypropyl cellulose | 5.4 g |
| Propylene glycol | 10.8 g |
| Talc | 5.4 g |
| Ethanol 96% | q.s |
| Water, purified | q.s |

Hydroxypropyl cellulose is dissolved in water. Ethylcellulose and ethanol are then added to the solution. Finally, propylene glycol and talc are added and the suspension is continuously stirred.

The coated sugar spheres from Step 1 are filled into a fluid-bed processor and preheated. The coated suspension prepared as indicated above is sprayed onto the coated sugar spheres. The pellets obtained thereby as then sieved to remove the agglomerates.

Step 3:

41 mg of coated pellets from step 2 are filled into capsule.

Example 3: Example of a Prolonged-Release Tablet Containing 10, 20, 40 and 80 mg Ketamine Hydrochloride The following tables show the compositions of prolonged-release tablet containing 10, 20, 40 and 80 mug ketamine hydrochloride. The coated pellets were similarly prepared to example 2.

Example 3.1 Prolonged-Release Tablet Containing 10 mg Ketamine Hydrochloride

| Component | Function | Amount/Unit | Quality Standard[#] |
|---|---|---:|---|
| Active Pellets | | | |
| Ketamine hydrochloride | Drug substance | 10.00 mg | Ph. Eur. |
| Sugar spheres (250-355 μm) | Carrier | 4.00 mg | Ph. Eur. |
| Hypromellose | Binder | 1.50 mg | Ph. Eur. |
| Ethanol 96% | Solvent | q.s | Ph. Eur. |
| Water, purified | Solvent | q.s | Ph. Eur. |
| Intermediate I Retard Coating | | 15.50 mg | |
| Ethylcellulose | Retarding polymer | 6.50 mg | Ph. Eur. |
| Hydroxypropylcellulose | Pore builder | 1.45 mg | Ph. Eur. |
| Propylene glycol | Plasticizer | 1.95 mg | Ph. Eur. |
| Talc | Glidant | 0.65 mg | Ph. Eur. |
| Ethanol (96%) | Solvent | q.s | Ph. Eur. |
| Water, purified | Solvent | q.s | Ph. Eur. |
| Intermediate II Final Blending | | 26.05 mg | |
| Carmellose sodium | Filler | 28.00 mg | Ph. Eur. |
| Cellulose, microcrystalline | Filler | 15.21 mg | Ph. Eur. |
| Magnesium stearate | Lubricant | 0.04 mg | Ph. Eur. |
| Silica, colloidal anhydrous | Glidant | 0.70 mg | Ph. Eur. |
| Core tablet Tablet coating | | 70.00 mg | |
| Opadry ® II White, consisting of: | Dye | 3.00 mg | In-house |

-continued

| Component | Function | Amount/Unit | Quality Standard[#] |
|---|---|---|---|
| Polyvinyl alcohol, Titanium dioxide, Macrogol, Talc | | | |
| Water, purified | Solvent | q.s | Ph. Eur. |
| Final weight of tablet | | 73.00 mg | |

Example 3.2 Prolonged-Release Tablet Containing 20 mg Ketamine Hydrochloride

| Component | Function | Amount/Unit | Quality Standard[#] |
|---|---|---|---|
| Active Pellets | | | |
| Ketamine hydrochloride | Drug substance | 20.00 mg | Ph. Eur. |
| Sugar spheres (250-355 μm) | Carrier | 8.00 mg | Ph. Eur. |
| Hypromellose | Binder | 3.00 mg | Ph. Eur. |
| Ethanol 96% | Solvent | q.s | Ph. Eur. |
| Water, purified | Solvent | q.s | Ph. Eur. |
| Intermediate I | | 31.00 mg | |
| Retard Coating | | | |
| Ethylcellulose | Retarding polymer | 13.00 mg | Ph. Eur. |
| Hydroxypropylcellulose | Pore builder | 2.90 mg | Ph. Eur. |
| Propylene glycol | Plasticizer | 3.90 mg | Ph. Eur. |
| Talc | Glidant | 1.30 mg | Ph. Eur. |
| Ethanol (96%) | Solvent | q.s | Ph. Eur. |
| Water, purified | Solvent | q.s | Ph. Eur. |
| Intermediate II | | 52.10 mg | |
| Final Blending | | | |
| Carmellose sodium | Filler | 56.00 mg | Ph. Eur. |
| Cellulose, microcrystalline | Filler | 30.42 mg | Ph. Eur. |
| Magnesium stearate | Lubricant | 0.08 mg | Ph. Eur. |
| Silica, colloidal anhydrous | Glidant | 1.40 mg | Ph. Eur. |
| Core tablet | | 140.00 mg | |
| Tablet coating | | | |
| Opadry ® II White, consisting of: Polyvinyl alcohol, Titanium dioxide, Macrogol, Talc | Dye | 5.40 mg | In-house |
| Opadry ® II Yellow, consisting of: Polyvinyl alcohol, Iron oxide yellow, Macrogol, Talc | Dye | 0.60 mg | In-house |
| Water, purified* | Solvent | 24.00 mg | Ph. Eur. |
| Final weight of tablet | | 146.00 mg | |

Example 3.3 Prolonged-Release Tablet Containing 40 mg Ketamine Hydrochloride

| Component | Function | Amount/Unit | Quality Standard[#] |
|---|---|---|---|
| Active Pellets | | | |
| Ketamine hydrochloride | Drug substance | 40.00 mg | Ph. Eur. |
| Sugar spheres (250-355 μm) | Carrier | 16.00 mg | Ph. Eur. |
| Hypromellose | Binder | 6.00 mg | Ph. Eur. |

| Component | Function | Amount/Unit | Quality Standard# |
|---|---|---|---|
| Ethanol 96% | Solvent | q.s | Ph. Eur. |
| Water, purified | Solvent | q.s | Ph. Eur. |
| Intermediate I Retard Coating | | 62.00 mg | |
| Ethylcellulose | Retarding polymer | 26.00 mg | Ph. Eur. |
| Hydroxypropylcellulose | Pore builder | 5.80 mg | Ph. Eur. |
| Propylene glycol | Plasticizer | 7.80 mg | Ph. Eur. |
| Talc | Glidant | 2.60 mg | Ph. Eur. |
| Ethanol (96%) | Solvent | q.s | Ph. Eur. |
| Water, purified | Solvent | q.s | Ph. Eur. |
| Intermediate II Final Blending | | 104.20 mg | |
| Carmellose sodium | Filler | 112.00 mg | Ph. Eur. |
| Cellulose, microcrystalline | Filler | 60.84 mg | Ph. Eur. |
| Magnesium stearate | Lubricant | 0.16 mg | Ph. Eur. |
| Silica, colloidal anhydrous | Glidant | 2.80 mg | Ph. Eur. |
| Core tablet Tablet coating | | 280.00 mg | |
| Opadry ® II White, consisting of: Polyvinyl alcohol, Titanium dioxide, Macrogol, Talc | Dye | 11.40 mg | In-house |
| Opadry ® II Red, consisting of: Polyvinyl alcohol, Iron oxide, Macrogol, Talc | Dye | 0.60 mg | In-house |
| Water, purified | Solvent | 48.00 mg | Ph. Eur. |
| Final weight of tablet | | 292.00 mg | |

Example 3.4 Prolonged-Release Tablet Containing 80 mg Ketamine Hydrochloride

| Component | Function | Amount/Unit | Quality Standard# |
|---|---|---|---|
| Active Pellets | | | |
| Ketamine hydrochloride | Drug substance | 80.00 mg | Ph. Eur. |
| Sugar spheres (250-355 µm) | Carrier | 32.00 mg | Ph. Eur. |
| Hypromellose | Binder | 12.00 mg | Ph. Eur. |
| Ethanol 96% | Solvent | q.s | Ph. Eur. |
| Water, purified | Solvent | q.s | Ph. Eur. |
| Intermediate I Retard Coating | | 124.00 mg | |
| Ethylcellulose | Retarding polymer | 52.00 mg | Ph. Eur. |
| Hydroxypropylcellulose | Pore builder | 11.60 mg | Ph. Eur. |
| Propylene glycol | Plasticizer | 15.60 mg | Ph. Eur. |
| Talc | Glidant | 5.20 mg | Ph. Eur. |
| Ethanol (96%) | Solvent | q.s | Ph. Eur. |
| Water, purified | Solvent | q.s | Ph. Eur. |
| Intermediate II Final Blending | | 208.40 mg | |
| Carmellose sodium | Filler | 112.00 mg | Ph. Eur. |
| Cellulose, microcrystalline | Filler | 233.68 mg | Ph. Eur. |
| Magnesium stearate | Lubricant | 0.32 mg | Ph. Eur. |
| Silica, colloidal anhydrous | Glidant | 5.60 mg | Ph. Eur. |
| Core tablet | | 560.00 mg | |

-continued

| Component | Function | Amount/Unit | Quality Standard[#] |
|---|---|---|---|
| Tablet coating | | | |
| Opadry ® II White, consisting of: Polyvinyl alcohol, Titanium dioxide, Macrogol, Talc | Dye | 20.00 mg | In-house |
| Water, purified | Solvent | 80.00 mg | Ph. Eur. |
| Final weight of tablet | | 580.00 mg | |

Example 4: In Vivo Pharmacokinetics, Metabolism and Safety

The pharmacokinetics, metabolism and safety of the prolonged-release dosage forms according to examples 3.1 to 3.4 were evaluated as follows.

A dose-escalation study was performed in five consecutive periods (7 days wash-out) in 15 healthy subjects (5 females, 20-25, BMI 19.4-27.6 kg/m2). The racemic analytes were measured using validated LC-MS/MS methods according to Hasan et al., 2017 (Hasan e: al., Quantitative chiral and achiral determination of ketamine and its metabolites by LC-MS/MS in human serum, urine and fecal samples, Journal of Pharmaceutical and Biomedical Analysis, 2017, 139, 87-97).

Therefore, the prolonged-release dosage forms according examples 3.1 to 3.4 were orally administered with 240 ml of table water in fasting state. In addition, 5 mg ketamine (in form of ketamine hydrochloride) solution was intravenously administered within 30 min in fasting state.

4.1 Pharmacokinetics

The pharmacokinetics of ketamine and its metabolites norketamine and hydroxynorketamine were measured and depicted in the following table 1. AUC stands for the area under the curve. $C_{max}$ stands for the maximum plasma concentration, $T_{max}$ stands for the time to $C_{max}$, F stands for absolute bioavailability, $T_{1/2}$ stands for the apparent terminal half-life, $AUC_{NK/K}$ for the ratio of $AUC_{NK}$ to $AUC_K$ and $AUC_{HNK/K}$ for the ratio of $AUC_{HNK}$ to $AUC_K$.

TABLE 1

Pharmacokinetic characteristics of ketamine after intravenous infusion (30 min) of 5 mg ketamine and oral administration of 10, 20, 40 and 80 mg ketamine PR tablets according to examples 3.1 to 3.4

| | | 5 mg i.v. | 10 mg p.o. | 20 mg p.o. | 40 mg p.o. | 80 mg p.o. |
|---|---|---|---|---|---|---|
| $AUC^1$ | ng × h/ml | 52.3 ± 12.2 | 13.4 ± 13.3 | 33.5 ± 35.8 | 63.5 ± 42.6 | 124 ± 72.9 |
| $AUC_{n-Ket}/AUC_{Ket}$ | | 1.79 ± 0.557 | 21.6 ± 14.2[#] | 16.9 ± 8.58[#]* | 14.9 ± 8.50[#]* | 14.0 ± 6.50[#]*[†] |
| $AUC_{HNK}/AUC_{Ket}$ | | 0.334 ± 0.128 | 7.33 ± 7.05[#] | 19.8 ± 16.4[#]* | 14.4 ± 8.99[#]* | 16.2 ± 7.93[#]*[‡] |
| $AUC_{DHNK}/AUC_{Ket}$ | | 0.446 ± 0.157 | 7.00 ± 6.19[#] | 6.65 ± 5.52[#] | 4.46 ± 3.19[#]*[†] | 3.68 ± 2.11[#]*[†] |
| $C_{max}$ | ng/ml | 29.9 ± 8.48 | 1.63 ± 1.33 | 3.70 ± 3.93 | 6.66 ± 4.25 | 11.8 ± 6.56 |
| $T_{max}$ | h | — | 5.34 ± 1.18 | 5.70 ± 0.649 | 5.87 ± 0.915 | 6.27 ± 0.594*[†] |
| F | % | — | 12.3 ± 10.7 | 15.3 ± 14.4* | 14.9 ± 8.94* | 14.6 ± 7.56* |
| $V_{ss}$ | l/kg | 6.58 ± 3.07 | — | — | — | — |
| $T_{1/2}$ | h | 5.89 ± 2.61 | 4.96 ± 1.25 | 6.74 ± 2.02* | 7.21 ± 1.56[#]* | 7.68 ± 1.43[#]*[†] |
| CL/F | l/min | 1.67 ± 0.380 | 22.3 ± 16.1[#] | 17.9 ± 11.4[#]* | 16.3 ± 11.1[#]* | 15.0 ± 8.93[#]* |
| $CL_R$ | ml/min | 33.6 ± 36.5 | 78.9 ± 32.2[#] | 70.2 ± 30.3[#]* | 67.3 ± 28.0[#] | 61.7 ± 23.3[#]* |
| $CL_M$ | ml/min | 268 ± 75.6 | — | — | — | — |
| $CL_{M, Nor Ket}$ | ml/min | 34.6 ± 14.4 | — | — | — | — |
| $CL_{M, HNK}$ | ml/min | 45.5 ± 8.65 | — | — | — | — |
| $CL_{M, DHNK}$ | ml/min | 188 ± 68.1 | — | — | — | — |
| $CL_{intestinal}$ | ml/min | 0.046 ± 0.097 | — | — | — | — |
| $A_{e, urine}$ | µg | 93.4 ± 71.6 | 44.8 ± 16.3 | 96.6 ± 39.3 | 209 ± 92.0 | 394 ± 166 |
| $A_{e, urine}$ | % | 1.87 ± 1.43 | 0.448 ± 0.163[#] | 0.483 ± 0.196[#] | 0.524 ± 0.230[#]* | 0.493 ± 0.208[#] |
| $A_{e, feces}$ | µg | 0.160 ± 0.343 | 131 ± 118 | 335 ± 401 | 557 ± 465 | 2050 ± 1770 |
| $A_{e, feces}$ | % | 0.003 ± 0.007 | 1.31 ± 1.18[#] | 1.68 ± 2.01[#] | 1.39 ± 1.16[#] | 2.56 ± 2.21[#]*[‡] |
| MRT | h | 4.68 ± 2.01 | 10.2 ± 1.41[#] | 11.2 ± 1.61[#] | 11.8 ± 1.27[#]* | 12.6 ± 1.10[#]*[‡] |
| MAT | h | — | 6.16 ± 1.40 | 7.11 ± 1.27 | 7.67 ± 1.16* | 8.45 ± 1.02*[†][‡] |

$p < 0.05$ (Wilcoxon test);
[#]vs. 5 mg i.v.,
*vs. 10 mg,
[†]vs 20 mg,
[‡]vs. 40 mg p.o.
[1]if $T_{last}$ = 60 h (24 h for 5 mg iv) then $AUC_{0-\infty}$, else $AUC_{0-60\ h(24\ h)}$

TABLE 2

Pharmacokinetic characteristics of norketamine after intravenous infusion (30 min) of 5 mg ketamine
and oral administration of 10, 20, 40 and 80 mg ketamine PR tablets according to examples 3.1 to 3.4

|  |  | 5 mg i.v. | 10 mg p.o. | 20 mg p.o. | 40 mg p.o. | 80 mg p.o. |
|---|---|---|---|---|---|---|
| $AUC^1$ | ng × h/ml | 95.0 ± 21.0 | 195 ± 68.7 | 392 ± 151 | 722 ± 188 | 1460 ± 404 |
| $AUC_{HNK}/AUC_{n\text{-}Ket}$ |  | 0.194 ± 0.093 | 0.342 ± 0.238 | 1.07 ± 0.594 | 0.953 ± 0.310 | 1.14 ± 0.328 |
| $C_{max}$ | ng/ml | 12.4 ± 2.67 | 15.8 ± 4.75 | 30.9 ± 10.1 | 54.9 ± 11.7 | 102 ± 24.3 |
| $T_{max}$ | h | 0.967 ± 0.303 | 4.87 ± 1.01[#] | 5.27 ± 0.923[#] | 5.80 ± 0.414[#*†] | 6.27 ± 0.458[#*†‡] |
| $T_{1/2}$ | h | 7.83 ± 1.46 | 8.11 ± 1.71 | 8.28 ± 1.52 | 8.06 ± 1.05 | 7.96 ± 0.920 |
| $A_{e,\,urine}$ | µg | 93.6 ± 23.9 | 173 ± 36.4 | 352 ± 120 | 664 ± 182 | 1280 ± 409 |
| $A_{e,\,urine}$ | % | 1.99 ± 0.507 | 1.83 ± 0.387 | 1.87 ± 0.636 | 1.76 ± 0.483 | 1.70 ± 0.543[#†] |
| $A_{e,\,feces}$ | µg | 2.16 ± 1.95 | 5.02 ± 3.97 | 9.55 ± 5.66 | 19.3 ± 17.8 | 39.4 ± 21.9 |
| $A_{e,\,feces}$ | % | 0.046 ± 0.041 | 0.053 ± 0.042 | 0.051 ± 0.030 | 0.051 ± 0.047 | 0.052 ± 0.029 |

$p < 0.05$ (Wilcoxon test);
[#] vs. 5 mg i.v.,
[*] vs. 10 mg,
[†] vs 20 mg,
[‡] vs. 40 mg p.o.
[1] if $T_{last} = 60$ h (24 h for 5 mg iv) then $AUC_{0\text{-}\infty}$, else $AUC_{0\text{-}60\,h(24\,h)}$

TABLE 3

Pharmacokinetic characteristics of hydroxynorketamine after intravenous
infusion (30 min) of 5 mg ketamine and oral administration of 10, 20,
40 and 80 mg ketamine PR tablets according to examples 3.1 to 3.4

|  |  | 5 mg i.v. | 10 mg p.o. | 20 mg p.o. | 40 mg p.o. | 80 mg p.o. |
|---|---|---|---|---|---|---|
| $AUC^1$ | ng × h/ml | 17.8 ± 7.97 | 61.8 ± 34.5 | 380 ± 185 | 657 ± 185 | 1610 ± 482 |
| $C_{max}$ | ng/ml | 1.32 ± 0.505 | 2.75 ± 1.15 | 20.3 ± 11.0 | 32.6 ± 9.38 | 75.5 ± 19.6 |
| $T_{max}$ | h | 3.57 ± 1.18 | 8.00 ± 1.73[#] | 8.00 ± 1.70[#] | 8.47 ± 2.77[#] | 8.40 ± 1.50[#] |
| $T_{1/2}$ | h | 7.92 ± 2.81 | 13.2 ± 7.77 | 9.23 ± 1.95 | 8.90 ± 1.42 | 9.27 ± 1.49 |
| $A_{e,\,urine}$ | µg | 145 ± 45.8 | 265 ± 70.1 | 540 ± 202 | 1100 ± 491 | 2270 ± 952 |
| $A_{e,\,urine}$ | % | 2.90 ± 0.916 | 2.65 ± 0.701 | 2.70 ± 1.01 | 2.74 ± 1.23 | 2.84 ± 1.19 |

$p < 0.05$ (Wilcoxon test);
[#] vs. 5 mg i.v.,
[*] vs. 10 mg,
[†] vs 20 mg,
[‡] vs. 40 mg p.o.
[1] if $T_{last} = 60$ h (24 h for 5 mg iv) then $AUC_{0\text{-}\infty}$, else $AUC_{0\text{-}60\,h(24\,h)}$

TABLE 4

Pharmacokinetic characteristics (as sum of R- and S-form) of dehydroxynorketamine
after intravenous infusion (30 min) of 5 mg ketamine and oral administration
of 10, 20, 40 and 80 mg ketamine PR tablets according to examples 3.1 to 3.4

|  |  | 5 mg i.v. | 10 mg p.o. | 20 mg p.o. | 40 mg p.o. | 80 mg p.o. |
|---|---|---|---|---|---|---|
| $AUC^1$ | ng × h/ml | 21.9 ± 3.88 | 50.7 ± 12.5 | 120 ± 44.2 | 182 ± 19.6 | 331 ± 62.5 |
| $C_{max}$ | ng/ml | 2.75 ± 0.776 | 4.04 ± 1.12 | 8.94 ± 3.31 | 12.4 ± 2.74 | 20.1 ± 4.12 |
| $T_{max}$ | h | 1.80 ± 0.528 | 4.80 ± 0.411[#] | 5.57 ± 0.998[#*] | 5.83 ± 1.21[#*] | 6.50 ± 1.24[#*†] |
| $T_{1/2}$ | h | 5.96 ± 1.85 | 8.20 ± 2.14[#] | 8.93 ± 2.72[#] | 9.43 ± 1.56[#*] | 8.90 ± 1.14[#] |
| $A_{e,\,urine}$ | µg | 516 ± 110 | 1040 ± 268 | 2210 ± 573 | 3630 ± 869 | 7280 ± 1559 |
| $A_{e,\,urine}$ | % | 10.3 ± 2.20 | 10.4 ± 2.68 | 11.0 ± 2.86 | 9.08 ± 2.17[†] | 9.09 ± 1.95[#†] |

$p < 0.05$ (Wilcoxon test);
[#] vs. 5 mg i.v.,
[*] vs. 10 mg,
[†] vs 20 mg,
[‡] vs. 40 mg p.o.
[1] if $T_{last} = 60$ h (24 h for 5 mg iv) then $AUC_{0\text{-}\infty}$, else $AUC_{0\text{-}60\,h(24\,h)}$

TABLE 5

Pharmacokinetic characteristics of (±)-ketamine after intravenous infusion (30 min) of 5 mg (±)-ketamine and oral administration of 10, 20, 40 and 80 mg ketamine PR tablets according to examples 3.1 to 3.4

|  | 5 mg i.v. | 10 mg p.o. | 20 mg p.o. | 40 mg p.o. | 80 mg p.o. |
|---|---|---|---|---|---|
| AUC (ng × h/ml) | 52.3 ± 12.2 | 13.4 ± 13.3 | 33.5 ± 35.8 | 63.5 ± 42.6 | 124 ± 72.9 |
| $C_{max}$ (ng/ml) | 29.9 ± 8.48 | 1.63 ± 1.33 | 3.70 ± 3.93 | 6.66 ± 4.25 | 11.8 ± 6.56 |
| $T_{max}$ (h) | — | 5.34 ± 1.18 | 5.70 ± 0.649 | 5.87 ± 0.915 | 6.27 ± 0.594*† |
| F (%) | — | 12.3 ± 10.7 | 15.3 ± 14.4* | 14.9 ± 8.94* | 14.6 ± 7.56* |
| $T_{1/2}$ (h) | 5.89 ± 2.61 | 4.96 ± 1.25 | 6.74 ± 2.02* | 7.21 ± 1.56#* | 7.68 ± 1.43#*† |
| $AUC_{NK/K}$ | 1.79 ± 0.557 | 21.6 ± 14.2# | 16.9 ± 8.58#* | 14.9 ± 8.50#* | 14.0 ± 6.50#*† |
| $AUC_{HNK/K}$ | 0.334 ± 0.128 | 7.33 ± 7.05# | 19.8 ± 16.4#* | 14.4 ± 8.99#* | 16.2 ± 7.93#*‡ | p < 0.05
vs. 5 mg i.v.,
*vs. 10 mg,
†vs 20 mg,
‡vs. 40 mg p.o. (Wilcoxon)

The maximum concentration ($C_{max}$) and the time of maximum concentration ($T_{max}$) were obtained directly from the measured concentration-time curves.

The area under the concentrations-time curve (AUC) was calculated with the measured data points from the time of administration until the last quantifiable concentration by the trapezoidal formula. The AUC was assessed up to the last sampling time above the limit of quantification and is extrapolated to infinity to obtain the AUC values.

Apparent Terminal half-life ($T_{1/2}$) was calculated by the following equation $T_{1/2} = \ln 2/\lambda_z$. The terminal elimination rate constant ($\lambda_z$) was evaluated from the terminal slope by log-linear regression analysis.

The absolute bioavailability (F) was calculated by the following equation $$F_{abs} = AUC_{oral}/AUC_{iv} \times dose_{iv}/dose_{oral}.$$

4.2 Safety

An Adverse event (AE) is any untoward medical occurrence in a patient or clinical investigation subject administered a pharmaceutical product which does not have necessarily a causal relationship with this treatment. An adverse event (AE) therefore can be any unfavorable and unintended sign including an abnormal laboratory (or vital. ECG etc.) finding, symptom or disease temporally associated with the use of a medicinal (investigational) product, whether or not related to the medicinal (investigational) product.

A serious adverse event (SAE) is defined as any untoward medical occurrence that at any dose
  results in death, or
  is life-threatening, or
  requires hospitalization or prolongation of existing hospitalization, or
  results in persistent or significant disability/incapacity, or
  is a congenital anomaly/birth defect Important medical reactions that may not be immediately life-threatening or result in death or hospitalization but may jeopardize the patient or may require intervention to prevent one of the other outcomes listed in the definition above should also be considered serious.

Examples of such events are intensive treatment in an emergency unit or at home for allergic bronchospasm, blood dyscrasia or convulsions that do not result in hospitalization, or development of drug dependency or drug abuse.

The term "life threatening", in the definition, refers to an event in which the patient was at risk of death at the time of the event; it does not refer to an event which hypothetically might have caused death if it were more severe.

Hospitalization for rehabilitation or surgery already planned before the start of the study period is not a serious AE. Such an event meets the definition of "no case".

An AE/SAE, the nature or severity of which is not consistent with the applicable product information (investigator's brochure, local product information sheet) is an Unexpected AE/SAE. Unexpected serious adverse reactions, which are suspected to be related to an investigational medicinal product, are called SUSARs (suspected unexpected serious adverse reaction).

Adverse events (AE) were detected both by a standardized questionnaire on tolerability and by querying the subjects at the scheduled times. Furthermore, the subjects were asked to report any AE spontaneously. 26 AEs occurred during the entire study; 10 AEs in Treatment A, 7 AEs in Treatment B, 1 AE in Treatment C, 2 AEs in Treatment D and 6 AEs in Treatment E. 7 AEs were considered by the clinical investigators to be not or unlikely related. 4 AEs were considered to be possibly related to the study medication and 11 to be probably related.

Dizziness (8 AEs), headache (4 AEs) and palpitations (3 AEs) belonged to the most frequent adverse events.

The results are depicted in the following table.

TABLE 6

Number and percent of subjects reporting adverse events by system organ class (SOC), preferred term (PT) and treatments for adverse events judged to be certainly, probably or possibly related to the study medication

| SOC | PT | Treatment A ketamine 5 mg i.v. | Treatment B ketamine 10 mg PR tablets | Treatment E ketamine 80 mg PR tablets |
|---|---|---|---|---|
| nervous system disorders | dizziness | 6 (40%) | 1 (7%) | — |
| cardiac disorders | palpitation | 1 (7%) | 1 (7%) | 1 (7%) |
| nervous system disorders | heaviness of head | — | 1 (7%) | — |

TABLE 6-continued

Number and percent of subjects reporting adverse events by system organ class (SOC), preferred term (PT) and treatments for adverse events judged to be certainly, probably or possibly related to the study medication

| SOC | PT | Treatment A ketamine 5 mg i.v. | Treatment B ketamine 10 mg PR tablets | Treatment E ketamine 80 mg PR tablets |
|---|---|---|---|---|
| gastrointestinal disorders | nausea | — | 1 (7%) | — |
| skin end subcutaneous tissue disorders | sweating/cold sweat | — | 1 (7%) | — |
| cardiac disorders | tachycardia | 1 (7%) | — | — |
| general disorders and administration site condition | weakness | — | 1 (7%) | — |

The invention claimed is:

1. A modified release dosage form for use in a method for the treatment of depression, to be orally administered, wherein the modified release dosage form is a prolonged-release dosage form comprising at least one prodrug of hydroxynorketamine wherein said prodrug is ketamine or pharmaceutically acceptable salts or solvates or mixtures thereof, wherein the oral administration of the prolonged-release dosage from results in plasma concentration profiles exhibiting a ratio of $AUC_{K/HNK}$ between 1:7 and 1:25.

2. A modified release dosage form for use in a method for the treatment of depression according to claim 1, wherein the oral administration of the prolonged-release dosage from results in a plasma concentration profiles exhibiting a ratio of $AUC_{K/NK}$ between 1:10 and 1:25.

3. A modified release dosage form for use in a method for the treatment of depression according to claim 1, wherein the prolonged-release dosage form contains ketamine in an amount of 5 to 400 mg.

4. A modified release dosage form for use in a method for the treatment of depression according to claim 1, wherein the prolonged-release dosage form is a matrix-controlled release dosage form, an osmotic controlled release dosage form or a multi particulate controlled release dosage form.

5. A modified release dosage form for use in a method for the treatment of depression according to claim 1, wherein the dosage form is a tablet.

6. A modified release dosage form for use in a method for the treatment of depression according to claim 4, wherein the administration of a single oral dosage form leads in-vivo to a $C_{max}$ of ketamine of 1 to 150 ng/ml.

7. A modified release dosage form for use in a method for the treatment of depression according to claim 4, wherein the administration of a single oral dosage form leads in-vivo to a $AUC_{0 \to \infty}$ of ketamine of 5 to 1000 ng·h/ml.

8. A modified release dosage form for use in a method for the treatment of depression according to claim 4, wherein $T_{max}$ of ketamine is 3 to 9 h.

9. A modified release dosage form for use in a method for the treatment of depression according to claim 4, wherein the prolonged-release dosage form is a matrix-controlled release dosage form, and wherein the dosage form comprises a matrix forming material in a concentration of between 10 and 95 wt. % based on the total weight of the dosage form.

10. A modified release dosage form for use in a method for the treatment of depression according to claim 9, wherein the matrix comprises synthetic and/or naturally occurring polymer(s).

11. A modified release dosage form for use in a method for the treatment of depression according to claim 4, wherein the dosage form further comprises a lubricant in a concentration of between 0.1 and 5 wt. % based on the total weight of of the dosage form.

12. A modified release dosage form for use in a method for the treatment of depression according to claim 4, wherein the prolonged-release dosage form is an osmotic controlled release dosage form selected from the one chamber system (elementary osmotic pump), two chamber system (push-pull system), asymmetric membrane technology (AMT) and extruding core system (ECS).

13. A modified release dosage form for use in a method for the treatment of depression according to claim 12, being an osmotic two chamber system with an active ingredient layer and an osmosis layer, wherein the osmosis layer comprises 30 to 90% of one or more osmopolymer(s) and 10 to 60% of an osmogene.

14. A modified release dosage form for use in a method for the treatment of depression according to claim 4, wherein the prolonged-release dosage form is a multi-particulate controlled release dosage form comprising a multitude of particles being pellets containing a core comprising a prodrug of hydroxynorketamine.

15. A modified release dosage form for use in a method for the treatment of depression according to claim 14, wherein the pellets further comprise a prolonged release control layer upon the core.

16. A modified release dosage form for use in a method for the treatment of depression according to claim 15, wherein the prolonged release control layer comprises one or more of cellulose esters, polyvinyl pyrrolidone, polyvinyl alcohol, polyvinyl acetate, polyvinyl chloride, nylon, polyamide, polyethylene oxide, polylactide-co-glycolide, alkyl celluloses, polymers and copolymers based on acrylate or methacrylate, polymers and copolymers based on acrylate or methacrylate.

17. A modified release dosage form for use in a method for the treatment of depression according to claim 1, wherein the treatment of depression is a long-term treatment.

18. A modified release dosage form for use in a method for the treatment of depression according to claim 11, wherein the long-term treatment lasts for at least one month.

* * * * *